United States Patent [19]

Barton et al.

[11] Patent Number: 4,501,703
[45] Date of Patent: Feb. 26, 1985

[54] PROCESS FOR PREPARING 2-ACETYLTHIOMETHYL-5-GUANIDINOPENTANOIC ACID

[75] Inventors: Russell L. Barton, Indianapolis; Stephen L. Briggs, Clayton; Gary A. Koppel, Indianapolis, all of Ind.

[73] Assignee: Eli Lilly and Company, Indianapolis, Ind.

[21] Appl. No.: 441,138

[22] Filed: Nov. 12, 1982

[51] Int. Cl.³ .......................................... C07C 153/017
[52] U.S. Cl. ................................................ 260/455 R
[58] Field of Search .................................... 260/455 R

[56] References Cited
PUBLICATIONS

Ondette, M. A., Condon, M. E., Reid, J., Sabo, E. F., Cheung, H. S., and Cushman, D. W., *Biochemistry 18,* 1427–1430 (1979).
Hugli, T. E., Gerard, C., Kawahara, M., Scheetz, M. E. *Molecular and Cellular Biochemistry 41,* 59–66 (1981).

*Primary Examiner*—Henry R. Jiles
*Assistant Examiner*—Robert C. Whittenbaugh
*Attorney, Agent, or Firm*—William C. Martens; Arthur R. Whale

[57] ABSTRACT

A process is described for preparing 2-acetylthiomethyl-5-quanidinopentanoic acid by treating 2-acetylthiomethyl-5-aminopentanoic acid with 1-quanyl-3,5-dimethylpyrazole in a medium comprising a hydroxylated solvent.

2 Claims, No Drawings

PROCESS FOR PREPARING 2-ACETYLTHIOMETHYL-5-GUANIDINOPENTANOIC ACID

BACKGROUND OF THE INVENTION (d,l)2-Mercaptomethyl-5-guanidinopentanoic acid is reported as a potent inhibitor of carboxypeptidase B [Ondetti, M. A., Condon, M. E., Reid, J., Sabo, E. F., Cheung, H. S., and Cushman, D. W., *Biochemistry* 18, 1427–1430 (1979)]. More recently, this compound has been shown to have excellent activity in inhibiting serum carboxypeptidase N (SCPN) [Hugli, T. E., Gerard, C., Kawahara, M., Scheetz, M. E., Barton, R., Briggs, S., Koppel, G., and Russell, S., *Molecular and Cellular Biochemistry* 41, 59–66 (1981)].

Ondetti et al, supra, details a multi-step sequence for the preparation of (d,l)2-mercaptomethyl-5-guanidinopentanoic acid. It is to a modification of the described method of preparation that this invention is directed. In the sequence described by Ondetti et al., supra, an intermediate, 2-acetylthiomethyl-5-guanidinopentanoic acid, is prepared by treating the corresponding 5-amino compound with 1-guanyl-3,5-dimethylpyrazole nitrate in dry N,N-dimethylformamide. After an extended period of reaction, only minor levels of conversion are experienced. It has now been discovered that the levels of conversion to the guanidino compound can be substantially increased and the reaction time substantially shortened by carrying out the reaction in accordance with the process of this invention.

SUMMARY OF THE INVENTION

Therefore, this invention is directed to a process for preparing 2-acetylthiomethyl-5-guanidinopentanoic acid, which comprises treating 2-acetylthiomethyl-5-aminopentanoic acid with 1-guanyl-3,5-dimethylpyrazole in a medium comprising a hydroxylated solvent.

DETAILED DESCRIPTION OF THE INVENTION

A schematic representation of the preparation of (d,l)2-mercaptomethyl-5-guanidinopentanoic acid from readily available starting materials is as follows:

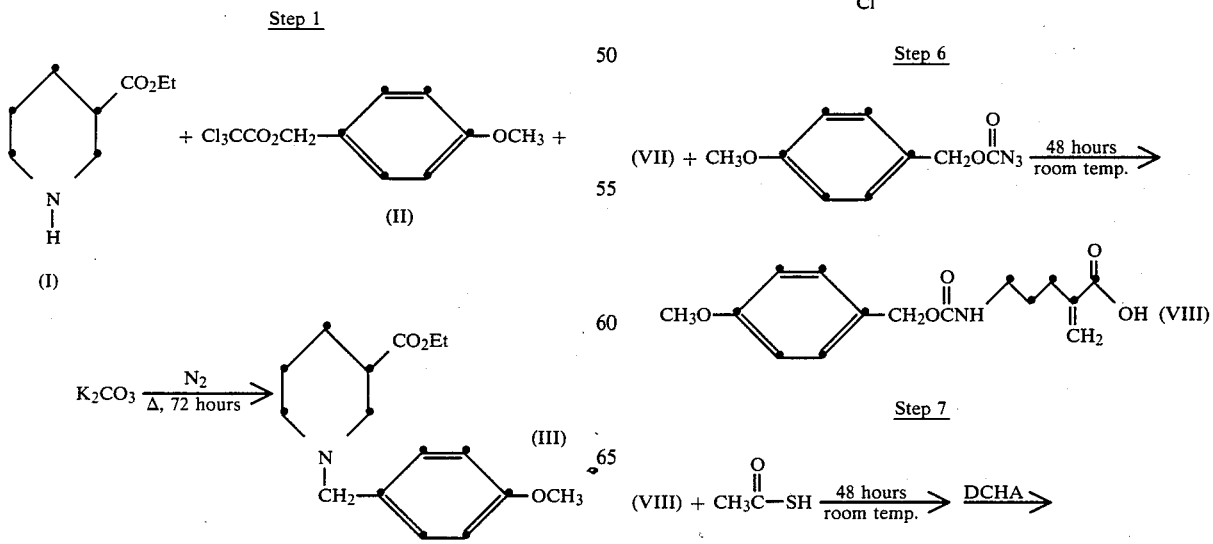

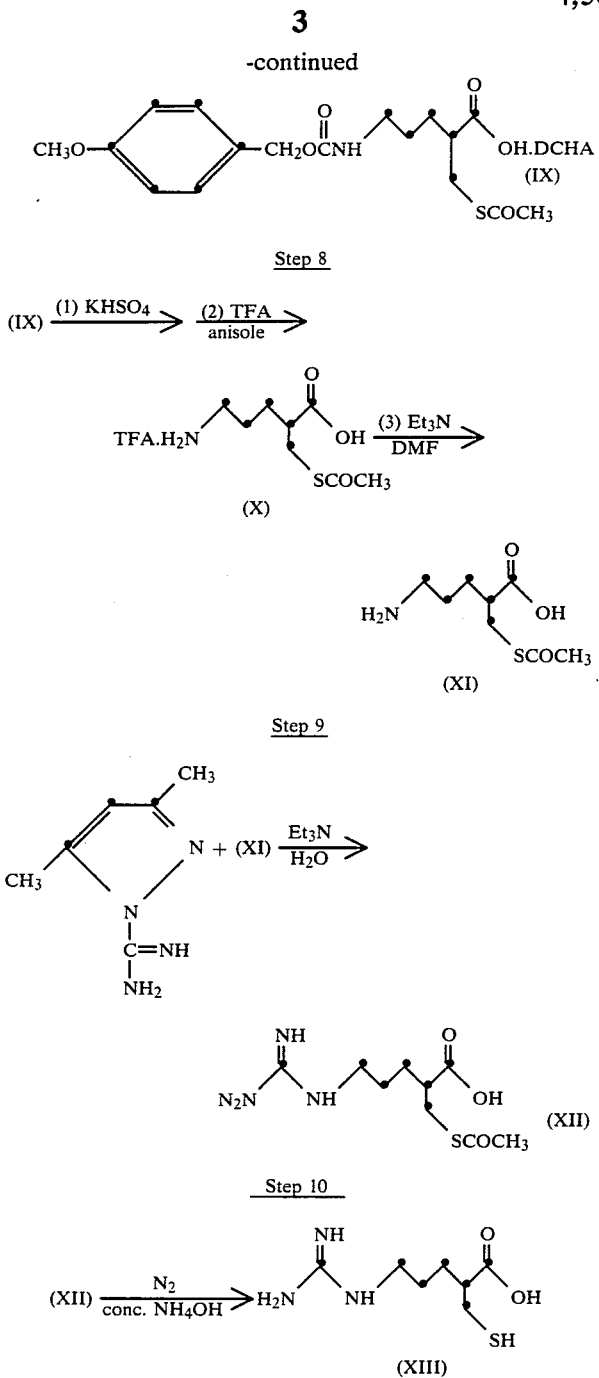

Step 8

Step 9

Step 10

The abbreviations used herein have the following meanings:
DCHA—Dicyclohexylamine
DMF—N,N-Dimethylformamide
Et—Ethyl
TFA—Trifluoroacetic acid The portion of the foregoing sequence that illustrates the process of this invention involves the conversion of 2-acetylthiomethyl-5-aminopentanoic acid (XI) to 2-acetylthiomethyl-5-guanidinopentanoic acid (XII) [Step 9]. In the Ondetti et al., supra, reference, this reaction is carried out under conditions which allow minimal conversion after an extended period for reaction. By the process of this invention, the product rapidly forms in high yield.

In reacting 2-acetylthiomethyl-5-aminopentanoic acid with 1-guanyl-3,5-dimethylpyrazole in accordance with the process of this invention, high levels of product are obtained by carrying out the reaction in a medium comprising a hydroxylated solvent. By "hydroxylated solvent" as used herein is meant, for example, water; alcohols, such as methanol, ethanol, n-propanol, isopropyl alcohol, and the like; glycols, such as ethylene glycol, propylene glycol, and the like; and other representative hydroxylated solvents. Of the above, water represents a highly preferred solvent for use in the process of this invention.

Typically, the process of this invention is carried out by dissolving 2-acetylthiomethyl-5-aminopentanoic acid and 1-guanyl-3,5-dimethylpyrazole, generally in an amount representing a large molar excess, in the selected hydroxylated solvent, usually water. To this solution then is added an excess of a base, typically triethylamine. The mixture is allowed to react at a slightly elevated temperature of from about 25° C. to about 50° C. for a period of up to about 10 hours or until the reaction is complete. The product, 2-acetylthiomethyl-5-guanidinopentanoic acid, is recovered by routine techniques, including, for example, extraction, lyophilization, and the like.

The following represents a detailed example of the preparation of (d,l)2-mercaptomethyl-5-quanidinopentanoic acid, including that portion of the overall preparation which illustrates the process of this invention.

EXAMPLE

A. Ethyl N-(p-methoxybenzyl)nipecotate hydrochloride (III)

To 7 liters of toluene were added 695 grams (4.4M) of ethyl nipecotate, 1304 grams (4.8M) of p-methoxybenzyl trichloroacetate, and 660 grams (4.8M) of potassium carbonate. The mixture was refluxed for 72 hours under a nitrogen atmosphere after which it was cooled, and the solvent was removed in vacuo. The resulting oil was dissolved in chloroform, and the solution was washed with 10% aqueous potassium carbonate followed by 10% aqueous hydrochloric acid. The solution then was dried over sodium sulfate and concentrated in vacuo. The resulting oil was triturated with ethyl ether, yielding 783 grams of the title compound as a solid.

B. N-(p-Methoxybenzyl)nipecotic acid (IV)

To a mixture of 1 liter of water and 5 liters of methanol were added 783 grams (2.5M) of the product from part A and 211 grams (5.3M) of sodium hydroxide. The mixture was stirred at room temperature for 17 hours after which the solvents were removed in vacuo. Toluene was added to the residue and removed in vacuo to obtain 1055 grams of crude title compound.

C. 1-(p-Methoxybenzyl)-3-methylene-2-piperidone (V)

A mixture of 800 grams (crude) of the product from part B, 6 liters of acetic anhydride, and 1 liter of triethylamine was refluxed for 4 hours. The solvents then were removed in vacuo. The resulting residue was dissolved in chloroform, and the chloroform solution was washed with water, dried over sodium sulfate, and concentrated in vacuo. The resulting oil was chromatographed over silica gel using a 1:1 mixture of hexane and ethyl acetate as eluant to obtain 219 grams of the title compound.

D. 3-Methylene-2-piperidone (VI)

A mixture of 219 grams (0.99M) of the product from part C, 276 grams (2.6M) of anisole and 3 liters of trifluoroacetic acid was refluxed for 48 hours under a nitrogen atmosphere. The solvents then were removed in vacuo, and the residue was chromatographed over silica gel using ethyl acetate as eluant to afford 115 grams of the title compound.

E. 2-Methylene-5-aminopentanoic acid, hydrochloride salt (VII)

To 8 liters of 6N hydrochloric acid were added 177 grams (1.59M) of the product as prepared in part E. The resulting mixture was refluxed for 40 hours after which it was cooled and extracted with methylene chloride. The aqueous layer then was concentrated in vacuo, toluene was added, and the solvents were again removed in vacuo. The resulting residue was recrystallized from isopropyl alcohol to obtain 44.6 grams of the title compound as a solid. A second crop yielded 26.9 grams of product as an oil.

F. 2-Methylene-5-(p-methoxybenzyloxycarbonyl-)aminopentanoic acid (VIII)

To a solution of 3.8 grams (53 mmol) of the product from part E in 100 ml. of water were added 6.4 grams (159 mmol) of magnesium oxide with stirring followed by a solution of 12.2 grams (59 mmol) of p-methoxybenzyloxycarbonyl azide in 100 ml. of p-dioxane. The resulting slurry was stirred at room temperature for two days. The mixture then was filtered through Hyflo and diluted with 200 ml. of ethyl acetate. AG50W-X2 Dowex 50 ion-exchange resin (200 ml. wet volume) was added, and the mixture was stirred at room temperature for 2 hours. The resin then was removed by filtration and washed with water. The filtrate layers were separated, and the aqueous layer was extracted twice with 200 ml. of ethyl acetate. The combined ethyl acetate solution was dried over magnesium sulfate and concentrated in vacuo to give 15.5 grams of the title compound as an oil.

G. 2-Acetylthiomethyl-5-(p-methoxybenzyloxycarbonyl-)aminopentanoic acid, dicyclohexylamine salt (IX)

To 15.5 grams of the oil containing the product from part F were added 50 ml. of thioacetic acid. The solution was allowed to stand at room temperature for 48 hours. The thioacetic acid then was removed in vacuo without addition of heat, and three portions of benzene were added and removed in vacuo to remove excess thioacetic acid. The resulting viscous oil was dissolved in ethyl ether, and the cloudy solution was treated with a slight excess (10%) of dicyclohexylamine. The mixture was cooled to less than 0° C., and crystals formed. The crystals were harvested to give 18.2 grams of the title compound.

H. 2-Acetylthiomethyl-5-aminopentanoic acid (XI)

The product from part G (12.5 grams; 22.7 mmol) was dissolved in 200 ml. of chloroform. The resulting solution was washed with two 200 ml. portions of 10% potassium bisulfate solution. The chloroform solution then was dried over magnesium sulfate and concentrated in vacuo.

The residue was dissolved in 18 ml. of anisole, and the mixture was cooled to 0°–5° C. Trifluoroacetic acid (115 ml.) was added dropwise over a 15 minute period, and the resulting solution was stirred at 0°–5° C. for 1 hour. The excess trifluoroacetic acid then was removed in vacuo. The residue was dissolved in water, and the aqueous solution was extracted with ethyl ether. The aqueous layer then was lyophilized to a pale yellow oil (X).

The yellow oil was dissolved in 65 ml. of dry N,N-dimethylformamide, and 8.6 ml. of triethylamine were added with stirring. A precipitate formed immediately The resulting mixture was filtered, and the solid was washed with dry N,N-dimethylformamide. The residue then was dried in vacuo overnight. The resulting dried clumps were dissolved in water and lyophilized to give 3.9 grams (19.0 mmol; 84% yield) of the title compound as a fluoculent off-white solid.

n.m.r.: (D$_2$O) 1.66 (m, 4, $\beta$ and $\gamma$ methylenes), 2.49 (m, 1, >CH—CO$_2$H), 2.99 (m, 4, —CH$_2$NH$_2$ and —CH$_2$SCOCH$_3$).

Analysis, Calculated for C$_8$H$_{15}$NO$_3$S (205): C, 46.81; H, 7.37; N, 6.82; S, 15.62. Found: C, 46.59; H, 7.07; N, 6.80; S, 15.77.

I. (dl)2-Mercaptomethyl-guanidinopentanoic acid (XIII)

To 100 ml. of 1.0N sodium hydroxide were added 4.9 g. (24.4 mmol.) of 1-guanyl-3,5-dimethylpyrazole nitrate. The resulting free base was extracted three times with 100 ml. of ethyl acetate. The ethyl acetate solutions were combined, dried over sodium sulfate, and concentrated in vacuo. The resulting residue was dissolved in 15 ml. of water, and 1.00 g. (4.9 mmol.) of the product from part H was added. The solution was degassed by evacuation, an argon atmosphere was introduced, and 1.4 ml. (9.8 mmol.) of triethylamine were added. The reaction apparatus was closed, and the solution was stirred at 40° C. for 3 hours. The aqueous solution was then washed four times with two-fold volumes of ethyl acetate. The aqueous solution was frozen and lyophilized to give 1.3 g. of a slightly impure, white solid, (mass spec shows on M-1, 246 ion; NMR good for desired product.)

The white solid (1.0 g.; 4.0 mmol.) was dissolved in 15 ml. of water, and the solution was degassed by evacuation. An argon atmosphere then was introduced. Concentrated NH$_4$OH (15.0 ml.) was added dropwise over a 5 minute period, and the solution was stirred at room temperature for 1 hour after completion of the addition. The reaction mixture then was degassed in vacuo for two hours, frozen, and lyophilized to a colorless syrup. The resulting syrup was dissolved in a minimum volume of 0.05M ammonium acetate buffer, pH 4.15, and the solution was applied to a BioRex 70 cation exchange column (3.5 cm.×38 cm.) equilibrated with the same buffer. Elution with the buffer was continued, and 20 ml. fractions were collected. All Sakaguchi positive fractions were pooled and lyophilized to give 0.310 g. of the title compound as a white solid, representing a total yield of 40% based upon the product from part H.

n.m.r.: (D$_2$O) 1.60 (m, 4, $\beta$ and $\gamma$ methylenes), 2.42 (m, 1, >CHCO$_2$H), 2.63 (m, 2, —CH$_2$SH), 3.22 (m, 2, —NH—CH$_2$—).

Mass Spectroscopy: 206 (M$^+$ +1), 205 (M$^+$), 174.

We claim:

1. A process for preparing 2-acetylthiomethyl-5-guanidinopentanoic acid, which comprises treating 2-acetylthiomethyl-5-aminopentanoic acid with 1-guanyl-3,5-dimethylpyrazole in a solvent comprising a hydroxylated solvent selected from the group consisting of water, alcohols, and glycols.

2. Process of claim 1, in which the hydroxylated solvent is water.

* * * * *